(12) United States Patent
Heun et al.

(10) Patent No.: US 8,323,804 B2
(45) Date of Patent: Dec. 4, 2012

(54) PARTIALLY CONJUGATED POLYMERS, THEIR REPRESENTATION AND THEIR USE

(75) Inventors: Susanne Heun, Bad Soden (DE); Amir Parham, Frankfurt (DE); Aurélie Ludemann, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 1038 days.

(21) Appl. No.: 11/720,901

(22) PCT Filed: Dec. 6, 2005

(86) PCT No.: PCT/EP2005/013043
§ 371 (c)(1),
(2), (4) Date: Jun. 5, 2007

(87) PCT Pub. No.: WO2006/061181
PCT Pub. Date: Jun. 15, 2006

(65) Prior Publication Data
US 2009/0226759 A1    Sep. 10, 2009

(30) Foreign Application Priority Data

Dec. 6, 2004 (EP) .................................... 04028865

(51) Int. Cl.
| | |
|---|---|
| C08F 14/16 | (2006.01) |
| C08G 61/02 | (2006.01) |
| C08G 79/08 | (2006.01) |
| C09K 11/06 | (2006.01) |
| H01L 51/54 | (2006.01) |

(52) U.S. Cl. ..... 428/690; 428/917; 257/40; 252/301.35; 528/397; 526/296

(58) Field of Classification Search .................. None
See application file for complete search history.

(56) References Cited

U.S. PATENT DOCUMENTS

| | | |
|---|---|---|
| 6,361,884 B1 | 3/2002 | Kreuder et al. |
| 2003/0091862 A1* | 5/2003 | Tokito et al. ............. 428/690 |
| 2005/0038223 A1 | 2/2005 | Becker et al. |
| 2006/0058524 A1 | 3/2006 | Falcou et al. |

FOREIGN PATENT DOCUMENTS

| | | |
|---|---|---|
| DE | 10241814 A1 | 3/2004 |
| WO | WO-90/13148 A1 | 11/1990 |
| WO | WO-97/20877 A2 | 6/1997 |
| WO | WO-00/46321 A1 | 8/2000 |
| WO | WO-02/77060 A1 | 10/2002 |
| WO | WO-03/020760 A1 | 3/2003 |

OTHER PUBLICATIONS

Cheng et al. Org. Lett. 2004, 6, 2381-2383. Date of web publication: Jun. 10, 2004.*
Cheng et al. Angew. Chem. Int. Ed. 2005, 44, 1118-1121. Date of web publication: Jan. 21, 2005.*

* cited by examiner

*Primary Examiner* — Lynda Salvatore
*Assistant Examiner* — Andrew K Bohaty
(74) *Attorney, Agent, or Firm* — Connolly Bove Lodge & Hutz LLP

(57) ABSTRACT

The present invention relates to partly conjugated spirobifluorene polymers which are linked in the polymer via both spiro molecule halves. The materials according to the invention display a purer emission color and a longer life than materials according to the prior art and are therefore better suited for use in polymeric organic light-emitting diodes.

22 Claims, No Drawings

PARTIALLY CONJUGATED POLYMERS, THEIR REPRESENTATION AND THEIR USE

RELATED APPLICATIONS

This application is a national stage application (under 35 U.S.C. §371) of PCT/EP2005/013043 filed Dec. 6, 2005, which claims benefit of European application 04028865.6 filed Dec. 6, 2004.

Wide-ranging research on the commercialization of display and lighting elements based on polymeric (organic) light-emitting diodes (PLEDs) has been carried out for some years. This development was treated by the basic developments disclosed in WO 90/13148. The first, simple products (small displays in a shaver and a mobile telephone from PHILIPS N.V.) have recently become available on the market. However, significant improvements in the materials used are still necessary in order for these displays to be genuinely competitive with the liquid crystal displays (LCDs) which currently dominate the market. To generate all three emission colours, it is necessary for particular comonomers to be copolymerized into the appropriate polymers (cf., for example, WO 00/46321, WO 03/020790 and WO 02/077060). In general, it is then possible, starting out from a blue-emitting base polymer ("backbone"), to generate the other two primary colours red and green.

Some of the conjugated polymers of the prior art display good properties when employed in PLEDs. However, despite the progress which has been achieved to date, these polymers still do not meet the requirements for high-quality applications. In particular, the life of the green-emitting polymers and especially the blue-emitting polymers is still not sufficient for many applications.

We presume that the electronic properties of the conjugated polymers are not yet optimal for balanced charge transport in the electronic device. As a result, the electron current or the hole current in the device is sometimes too large, and a balanced charge equilibrium cannot be established. A further disadvantage is the statistically broad distribution of effective conjugation lengths in the polymer, which leads to polymer sections of undefined length and relatively broad-band emission and thus low colour purity.

Despite the progress achieved to date, there is still a considerable need for improvements in corresponding materials. In particular, there is still a need for significant improvement in the following fields:

The efficiency at high luminances is still in need of improvement for all colours. This is of critical importance for use in, in particular, Passive Matrix (PM) displays: in these PM displays, each individual pixel is controlled for only a fraction of the time (this fraction is referred to as the multiplex rate (MUX)). An MUX-64 or MUX-128 display means that each individual pixel is controlled for only $1/64$ or $1/128$, respectively, of the total time. To obtain the desired brightness despite this, the respective pixel has to emit more brightly by the same factor, i.e. in these cases 64 or 128) in this short time than would actually be necessary for the desired brightness. If, for example, a pixel is to be operated at an average luminance of 200 cd/m$^2$, it is necessary to achieve 12 800 or even 25 600 cd/m$^2$ for the short period. Due to the sluggishness of the human eye, the observer then, if the display is controlled appropriately, has the impression of the average brightness value. The problem with this control is that the polymers utilized hitherto have a strong dependence of the efficiency on the brightness required. This results in great difficulties for PM displays.

The operating life, especially in the case of BLUE-emitting polymers and PM control, is still in need of significant improvement in order to meet market requirements.

WO 97/20877 and EP 0882082 describe partly conjugated spirobifluorene polymers which are linked via the 2,2' positions of the spirobifluorene units. An advantage of these polymers is said to be, in particular, the excellent processability. However, all that is said about the electronic properties is that electroluminescence is observed on application of a sufficiently high voltage, without details of voltage, efficiency and life being given. The use of 2,2'-linked spirobifluorene units is also described in some publications, e.g. by R. D. Miller et al. (*Polymer Preprints* 2002, 43, 116-117), F.-I. Wu et al. (*J. Mater. Chem.* 2002, 12, 2893-2897) and B. Huang et al. (*Chem. Lett.* 2004, 33, 1376-1377). However, particularly good suitability of these polymers for organic electroluminescent devices can be seen in none of these publications.

It has now surprisingly been found that partly conjugated polymers which are linked via the two halves of spirobifluorene which are not conjugated with one another but via positions other than the 2,2' positions have very good properties which are superior to the prior art. In particular, these polymers display better electroluminescence properties than comparable polymers which are linked via the 2,2' positions of spirobifluorene. This applies in particular to the life in the case of PM control but also to the emission colour, the current-voltage curves and the efficiency of the polymers. This is a surprising and unexpected result. These polymers and their use in organic electronic devices are therefore subject matter of the present invention.

The invention provides polymers comprising at least 1 mol %, preferably at least 5 mol %, particularly preferably at least 10 mol %, of a first repeating unit of the formula (1),

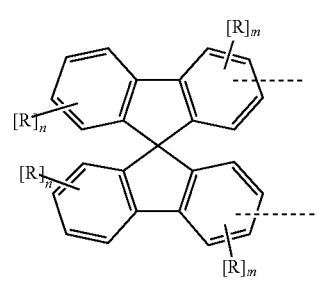

Formula (1)

where the symbols and indices used have the following meanings:

R is identical or different on each occurrence and is in each case F, Cl, Br, I, CN, NO$_2$, OH, N(R$^1$)$_2$, Si(R$^1$)$_3$, B(R$^1$)$_2$, a straight-chain alkyl, alkoxy or thioalkoxy group having from 1 to 40 carbon atoms or a branched or cyclic alkyl, alkoxy or thioalkoxy group which has from 3 to 40 carbon atoms and in which one or more nonadjacent carbon atoms may also be replaced by —CR$^1$=CR$^1$—, —C≡C—, —NR$^1$—, —O—, —S—, —CO—O—, C=O, P(=O)R$^1$, SO, SO$_2$ or —O—CO—O— and one or more H atoms may also be replaced by fluorine, or an aromatic or heteroaromatic ring system which has from 5 to 40 aromatic ring atoms and may also be substituted by one or more nonaromatic radicals R; or a combination of 2, 3, 4 or 5 of the abovementioned groups; with two or more of the radicals R together also being able to form an aliphatic or aromatic, monocyclic or polycyclic ring system;

$R^1$ is identical or different on each occurrence and is in each case H or an aliphatic or aromatic hydrocarbon radical having from 1 to 20 carbon atoms;

n is identical or different on each occurrence and is in each case 0, 1, 2, 3 or 4;

m is identical or different on each occurrence and is in each case 0, 1, 2 or 3;

the bonds shown as broken lines indicate the linkage in the polymer;

with the proviso that linkage is not via the 2,2' positions;

and at least 1 mol % of a second repeating unit which is either identical to a repeating unit of the formula (1) or is different therefrom.

The positions on the spirobifluorene are shown below in the interests of clarity:

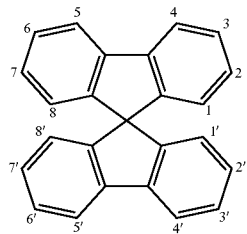

For the purposes of the present invention, a $C_1$-$C_{40}$-alkyl group in which individual H atoms or $CH_2$ groups may also be replaced by the abovementioned groups is particularly preferably one of the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$-$C_{40}$-alkoxy group is particularly preferably methoxy, ethoxy, n-propoxy, i-propoxy, n-butoxy, i-butoxy, s-butoxy, t-butoxy or 2-methylbutoxy. An aromatic or heteroaromatic ring system which has 5-40 aromatic ring atoms and may additionally be substituted by the above-mentioned radicals R and may be linked via any positions to the aromatic or heteroaromatic is, in particular, a group derived from benzene, naphthalene, anthracene, phenanthrene, pyrene, chrysene, perylene, fluoranthene, naphthacene, pentacene, benzpyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzpyrimidine, quinoxaline, 175-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Even though this is indicated by the description, it will at this point be explicitly stated once more that the structural units of the formula (1) can be unsymmetrically substituted, i.e. that different substituents R can be present in one unit and these can also be bound in different positions.

For the purposes of the present invention, an aromatic or heteroaromatic ring system is a system which does not necessarily comprise only aromatic or heteroaromatic groups; rather, a plurality of aromatic or heteroaromatic groups in the system may also be interrupted by a short nonaromatic unit (<10% of the atoms other than H, preferably <5% of the atoms other than H), for example $sp^3$-hybridized C, O, N, etc. Thus, for example, systems such as 9,9'-spirobifluorene, 9,9-diarylfluorene, triarylamine, etc., are also regarded as aromatic systems for the purposes of the present invention.

Units of the formula (1) can have two enantiomeric forms. Within the scope of the invention, it is equally possible to use the racemate, i.e. the 1:1 mixture of the two enantiomers, or one of the two enantiomers in enriched or isolated form.

Preference is given to units of the formula (1) in which the symbols and indices have the following meanings:

R is identical or different on each occurrence and is in each case F, CN, $NO_2$, OH, $N(R^1)_2$, a straight-chain alkyl, alkoxy or thioalkoxy group having from 1 to 20 carbon atoms or a branched or cyclic alkyl, alkoxy or thioalkoxy group which has from 3 to 40 carbon atoms and in which one or more nonadjacent carbon atoms may also be replaced by —$CR^1$=$CR^1$—, —C≡C—, —$NR^1$—, —, —S—, C=O or P(=O)$R^1$ and one or more H atoms may also be replaced by fluorine, or an aromatic or heteroaromatic ring system which has from 5 to 30 aromatic ring atoms and may also be substituted by one or more nonaromatic radicals R; or a combination of 2, 3 or 4 of the abovementioned groups; with two or more of the radicals R together also being able to form an aliphatic or aromatic, monocyclic or polycyclic ring system;

$R^1$ is as described above;

n is identical or different on each occurrence and is in each case 0, 1, 2 or 3;

m is identical or different on each occurrence and is in each case 0, 1 or 2.

Particular preference is given to units of the formula (1) in which the symbols and indices have the following meanings:

R is identical or different on each occurrence and is in each case F, $N(R^1)_2$, a straight-chain alkyl or alkoxy group having from 1 to 10 carbon atoms or a branched or cyclic alkyl or alkoxy group which has from 3 to 10 carbon atoms and in which one or more nonadjacent carbon atoms may also be replaced by —$CR^1$=$CR^1$—, —C≡C—, —O— or C=O and one or more H atoms may also be replaced by fluorine, or an aromatic or heteroaromatic ring system which has from 5 to 20 aromatic ring atoms and may also be substituted by one or more nonaromatic radicals R; or a combination of two or three of the abovementioned groups; with two or more of the radicals R together also being able to form an aliphatic or aromatic, monocyclic or polycyclic ring system;

R¹ is as described above;
n is identical or different on each occurrence and is in each case 0, 1 or 2;
m is identical or different on each occurrence and is in each case 0 or 1.

Furthermore, preference is given to units of the formula (1) which are symmetrically substituted on the two spiro molecule halves. This preference is due to the greater ease with which the monomers can be synthesized.

According to the invention, the units of the formula (1) can be linked in various ways in the polymer. Preference is given to linkage via identical positions on the two spiro molecule halves. This preference is once again due to the greater ease with which the corresponding monomers can be synthesized. A preferred embodiment of the invention therefore provides for linkage to be via the 1,1' positions, via the 3,3' positions or via the 4,4' positions. A particularly preferred embodiment of the invention provides for linkage to be via the 1,1' positions or via the 4,4' positions. Very particular preference is given to linkage via the 4,4' positions.

It follows from the type of linkage that the units of the formula (1) are bound into the main chain of the polymer and that the units of the formula (1) lead to a kink in the polymer chain, since the sp³-hybridized spiro carbon atom which is responsible for the orthogonal linkage of the two spiro molecule halves is located between the two bonds to the polymer.

The polymers of the invention can be partly conjugated or nonconjugated. Completely conjugated polymers are not possible here, since the units of the formula (1) always represent an interruption to the conjugation. In a preferred embodiment of the invention, the polymer is a partly conjugated polymer. The polymer particularly preferably contains no further units which interrupt the conjugation of the polymer apart from units of the formula (1).

For the purposes of the present invention, a partly conjugated polymer is a polymer in which relatively long conjugated sections in the main chain are interrupted by nonconjugated sections which, as mentioned above, are preferably produced by units of the formula (1). These conjugated sections are produced by sp²-hybridized (or else sp-hybridized) carbon atoms which may also be replaced by appropriate heteroatoms, which in the simplest case means alternating presence of double (or triple) and single bonds. Furthermore, for the purposes of the present patent application, systems in which, for example, arylamine units and/or particular heterocycles (i.e. conjugation via N, O or S atoms) and/or organometallic complexes (i.e. conjugation via the metal atom) are present in the main chain will likewise be regarded as conjugated. On the other hand, units such as simple alkylene bridges, (thio)ether, ester, amide or imide linkages will be defined as nonconjugated segments.

The polymers of the invention preferably comprise further structural elements which are different from units of the formula (1) in addition to units of the formula (1), and are thus to be regarded as copolymers. The further structural elements are preferably conjugated. Here, reference may also be made, in particular, to the relatively comprehensive listings in WO 02/077060, WO 05/014689 and the references cited therein. These further structural units can, for example, come from the classes described below:

Group 1. Aromatic Units which Usually Represent the Polymer Backbone:

Units of this group are aromatic, carbocyclic structures which have from 6 to 40 carbon atoms and may be substituted or unsubstituted, with possible substituents being the radicals R mentioned above. Fluorene derivatives (e.g. EP 0842208, WO 99/54385, WO 00/22027, WO 00/22026, WO 00/46321) are suitable. Furthermore, spirobifluorene derivatives (e.g. EP 0707020, EP 0894107, WO 03/020790) are also possible. Polymers comprising a combination of the two monomer units mentioned above have also been proposed (WO 02/077060). WO 05/014689 describes dihydrophenanthrene derivatives. Furthermore, cis- or trans-indenofluorene derivatives (e.g. WO 04/041901, WO 04/113412) and also 1,4-phenylene derivatives, 4,4'-biphenylene derivatives, 4,4"-terphenylene derivatives, 2,7- or 3,6-phenanthrene derivatives (e.g. DE 0102004020298.2), dihydropyrene or tetrahydropyrene derivatives and further aromatic structures which will not be explicitly mentioned are also possible. Units of group 1 are thus preferably selected from the group consisting of fluorene derivatives, spirobifluorene derivatives, dihydrophenanthrene derivatives, cis- or trans-indenofluorene derivatives, 174-phenylene derivatives, 4,4'-biphenylene derivatives, 4,4"-terphenylene derivatives, 2,7- or 3,6-phenanthrene derivatives, dihydropyrene and tetrahydropyrene derivatives. Particularly preferred units from this group are selected from among spirobifluorene, fluorene, dihydrophenanthrene, cis-indenofluorene, trans-indenofluorene and 2,7-phenanthrene which may be substituted by R or be unsubstituted.

Group 2: Units which Alter the Morphology or the Emission Colour:

Structural elements which can influence the morphology and also the emission colour of the resulting polymers are also possible. These are preferably selected from the group consisting of fused aromatic structures which have from 6 to 40 carbon atoms and may unsubstituted or substituted by R and also tolane, stilbene and bisstyrylarylene derivatives, e.g. 1,4-naphthylene, 1,4- or 9,10-anthrylene, 1,6- or 2,7- or 4,9-pyrenylene, 3,9- or 3,10-perylenylene, 4,4'-bi-1,1'-naphthylene, 4,4'-tolanylene, 4,4'-stilbenzylene or 4,4"-bisstyrylarylene derivatives.

Group 3: Units which Increase the Hole Injection and/or Transport Properties of the Polymers:

These are generally aromatic amines or phosphines or electron-rich heterocycles and are preferably selected from the group consisting of R-substituted or unsubstituted triarylamines, benzidines, N,N,N',N'-tetraaryl-para-phenylenediamines, triarylphosphines, phenothiazines, phenoxazines, dihydrophenazines, thianthrenes, dibenzo-p-dioxins, phenoxathiines, carbazoles, azulenes, thiophenes, pyrroles, furans and further O-, S- or N-containing heterocycles having a high HOMO (HOMO=highest occupied molecular orbital). These units can be incorporated into the main chain or into the side chain of the polymer. Depending on the structure, the polymer backbone is also able to conduct holes sufficiently well for it not to be absolutely necessary for units of group 3 to be present.

Group 4: Units which Increase the Charge Injection and/or Transport Properties of the Polymers:

These are generally electron-poor aromatics or heterocycles and are preferably selected from the group consisting of R-substituted or unsubstituted pyridines, pyrimidines, pyridazines, pyrazines, triazines, oxadiazoles, quinolines, quinoxalines and phenazines and also compounds such as triarylboranes and further O—, S— or N-containing heterocycles having a low LUMO (LUMO=lowest unoccupied molecular orbital). Depending on the structure, the polymer backbone is also able to conduct electrons well, so that it is not absolutely necessary for units of group 4 to be present.

Group 5: Units which have Combinations of Individual Units of Group 3 and Group 4:

It can also be preferred for units in which structures which increase hole mobility and which increase electron mobility are bound directly to one another, i.e. structures from the abovementioned groups 3 and 4, to be present in the polymers of the invention. Many of these units shift the emission colour into the green, yellow or red; their use is thus also suitable, for example, for generating other emission colours from originally blue-emitting polymers.

Group 6: Units which Emit Light from the Triplet State:

Structural units of this group can emit light from the triplet state with high efficiency even at room temperature and thus display electrophosphorescence instead of electrofluorescence. Compounds which are suitable for this purpose are firstly compounds which contain heavy atoms having an atomic number of more than 36. Compounds which contain d or f transition metals which meet this condition are particularly suitable. Very particular preference is given to structural units containing elements of groups 8 to 10 (Ru, Os, Rh, Ir, Pd, Pt). These metal complexes can be incorporated into the main chain and/or into the side chain of the polymer. The incorporation of such metal complexes at branching points in the polymer, as described, for example, in DE 102004032527.8, has also been found to be useful. If units from group 6 are present, it can be preferred that units from group 7 are present at the same time. However, even without such units from group 7, very good results and very high efficiencies can be achieved using triplet emitters.

Group 7: Units which Aid Transfer from the Singlet State to the Triplet State:

When using triplet emitters, the supporting use of further structural elements which improve transition from the singlet state to the triplet state and thus the electrophosphorescence properties can be preferred. Structural elements which are suitable for this purpose are, for example, carbazole units as described in WO 04/070772 and WO 04/113468, also, for example, keto, phosphine oxide, sulphoxide or sulphone units as described in WO 05/040302 or silane units as described in the unpublished patent application DE 102004023278.4. The units are thus preferably selected from the group consisting of carbazole units, bridged carbazole units, keto, phosphine oxide, sulphoxide or sulphone units and silane units.

Preference is given to polymers which comprise one or more units selected from the groups 1 to 7 in addition to structural units of the formula (1). It can in this case also be advantageous for more than one structural unit from one of the groups 1 to 7 to be simultaneously present.

Particular preference is given to polymers comprising units from group 1 in addition to units of the formula (1), very particularly preferably at least 30 mol % of such units. Particular preference is also given to polymers comprising units from group 2 and/or 3 in addition to units of the formula (1), very particularly preferably at least 5 mol % of such units.

The required solubility of the polymers is achieved, in particular, by means of the substituents on various repeating units, both the substituents R and $R^1$ on units of the formula (1) and substituents R on the other repeating units.

Preference is given to a proportion of 1-100 mol % of units of the formula (1). Particular preference is given to a proportion of 5-70 mol % of units of the formula (1), very particularly preferably a proportion of 10-50 mol %.

The polymers of the invention are either homopolymers composed of units of the formula (1) or copolymers. Copolymers according to the invention can potentially have one or more further structures from the abovementioned groups 1 to 7 in addition to one or more structures of the formula (1). In this case, the interruption to conjugation due to units of the formula (1) can occur in the vicinity of each of the structural units of groups 1 to 7. The copolymers of the invention can have random, alternating or block structures or can have a plurality of these structures in an alternating sequence. The way in which copolymers having block structures can be obtained is described, for example, in WO 05/014688. It may likewise be emphasized at this point that the polymer does not necessarily have to have a linear structure, but can also be branched or have dendritic structures.

The polymers of the invention generally have from 10 to 10 000 repeating units, preferably from 20 to 5000 repeating units, particularly preferably from 50 to 2000 repeating units.

The polymers of the invention are generally prepared by polymerization of one or more types of monomer of which at least one monomer leads to units of the formula (1) in the polymer. There are in principle many appropriate polymerization reactions.

However, some types which lead to C—C or C—N linkages have been found to be particularly useful:
(A) Suzuki polymerization;
(B) Yamamoto polymerization;
(C) Stille polymerization;
(D) Hartwig-Buchwald polymerization.

The way in which the polymerization can be carried out according to these methods and the way in which the polymers can be separated off from the reaction medium and purified is described, for example, in WO 03/048225 and WO 04/022626. The way in which particularly pure polymers can be obtained is described, for example, in EP 04023475.9.

The synthesis of the polymers requires the corresponding monomers. For information on the synthesis of units of groups 1 to 7, reference may be made to the abovementioned literature.

Monomers which lead to structural units of the formula (1) in polymers according to the invention are corresponding spirobifluorene derivatives which have suitable functions which allow this monomer unit to be built into the polymer on suitable positions on both halves of the molecule, in particular in the 4,4' positions or in the 1,1' positions. Particularly useful functions for the polymerization are halogens, in particular bromine, or sulphonates or, in the case of Suzuki polymerization, boronic acid derivatives or, in the case of Stille polymerization, trialkyltin derivatives. The synthesis of 4,4'-dibromospirobifluorene derivatives has been described by X. Cheng et al. (Org. Lett. 2004, 6, 2381-2383). This synthesis also makes it possible to introduce substituents in the 1,1' positions. The boronic acid derivatives can likewise be produced from the bromine derivatives by means of standard reactions with which a person skilled in the art of organic synthesis is familiar.

Appropriate monomers for the polymerization via the 1,1' positions can likewise be produced from the above-described 4,4'-dibromo-1,1'-dialkoxy derivatives. For this purpose, the 4,4' positions are firstly blocked by reaction of the bromine (for example by coupling with a boronic acid derivative or by reduction). The alkoxy groups are converted into reactive functional groups, for example into triflate groups, which can either be used directly in the polymerization or can be converted, for example, into a boronic acid derivative in a palladium-catalysed reaction.

The invention further provides bifunctional monomeric compounds of the formula (2),

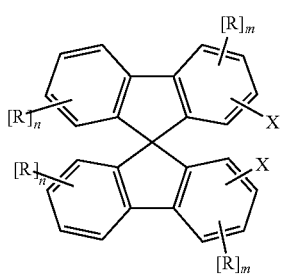

Formula (2)

where $R^1$, n and m are as defined above and the further symbols and indices have the following meanings:

X is identical or different on each occurrence and is in each case a group which copolymerizes under the conditions of the C—C or C—N coupling reaction;

R is identical or different on each occurrence and is in each case CN, $NO_2$, OH, $N(R^1)_2$, $Si(R^1)_3$, $B(R^1)_2$, a straight-chain alkyl, alkoxy or thioalkoxy group having from 1 to 40 carbon atoms or a branched or cyclic alkyl, alkoxy or thioalkoxy group which has from 3 to 40 carbon atoms and in which one or more nonadjacent carbon atoms may also be replaced by —$CR^1$=$CR^1$—, —C≡C—, —$NR^1$—, —O—, —S—, —CO—O—, C=O, P(=O)$R^1$, SO, $SO_2$ or —O—CO—O— and one or more H atoms may also be replaced by fluorine, an aromatic or heteroaromatic ring system having from 5 to 40 aromatic ring atoms which may also be substituted by one or more nonaromatic radicals R; or a combination of 2, 3, 4 or 5 of the abovementioned groups; with two or more of the radicals R together also being able to form an aliphatic or aromatic, monocyclic or polycyclic ring system;

with the following compound being excluded from the invention:

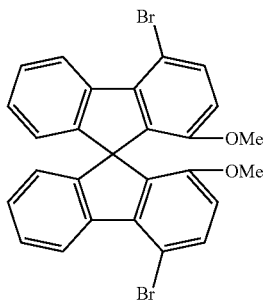

and also with the proviso that the two groups X are not bound in the 2 and 2' positions.

X is preferably selected from among Cl, Br, I, O-tosylate, O-triflate, O—$SO_2R^1$, $B(OR^1)_2$ and $Sn(R^1)_3$, particularly preferably from among Br, O-triflate and $B(OR^1)_2$, where $R^1$ is as defined above and two or more radicals $R^1$ together may also form a ring system.

In addition, the use of the polymer of the invention not as a pure substance but as a mixture (blend) with any further polymeric, oligomeric, dendritic and/or low molecular weight substances can be preferred. These substances can, for example, improve the electronic properties or be emitters themselves. Thus, for example, a preferred embodiment of the invention comprises addition of a compound which can emit light with high efficiency from the triplet state at room temperature, so that the mixture is then capable of emitting light from the triplet state with high efficiency. Such compounds have been described above as further structural elements for the polymer. The same preferences as described above apply to the added compounds. However, electronically inert blend constituents can also be useful, for example for controlling the viscosity of a solution or the morphology of the film formed. Such blends are therefore also provided by the present invention.

The invention further provides solutions and formulations comprising one or more polymers or blends according to the invention in one or more solvents. The way in which polymer solutions can be prepared is described, for example, in WO 02/072714, WO 03/019694 and the references cited therein. These solutions can be used for producing thin polymer layers, for example by surface coating methods (e.g. spin coating) or by printing processes (e.g. inkjet printing).

The polymers and blends of the invention can be used in PLEDs. The way in which PLEDs can be produced is described comprehensively as a general process in WO 04/037887, and this process can be adapted appropriately for the particular case. As described above, the polymers of the invention are very particularly suitable as electroluminescence materials in PLEDs or displays produced in this way.

For the purposes of the invention, electroluminescence materials are materials which can be used as active layer in a PLED. The term active layer means that the layer is capable of radiating light on application of an electric field (light-emitting layer) and/or that it improves the injection and/or transport of positive and/or negative charges (charge injection layer or charge transport layer).

The invention therefore also provides for the use of a polymer or blend according to the invention in a PLED, in particular as electroluminescence material.

The invention likewise provides a PLED having one or more active layers of which at least one comprises one or more polymers or blends according to the invention. The active layer can, for example, be a light-emitting layer and/or a transport layer and/or a charge injection layer.

Compared to the polyspirobifluorenes described in WO 03/020790, which are linked via the 2,7 positions in the polymer, and compared to polyspirobifluorenes as described in WO 97/20877 and EP 0882082, which are linked via the 2,2' positions, which are here named as nearest prior art, the polymers of the invention have the following surprising advantages:

(1) The life under PM control is higher than in the case of comparable polymers which have a similar composition but do not contain any units of the formula (1), instead having their spirobifluorenes linked via the 2,7 or, in particular, the 2,2' positions. An improvement in the life is of tremendous importance in practical use, since, particularly in the case of blue- and green-emitting polymers, an insufficient life has hitherto been the greatest obstacle to industrial use. This result is surprising compared to conjugated polymers based on 2,7-linked spirobifluorenes, since it has hitherto been assumed that a high degree of conjugation is a necessary prerequisite for a long life. The improved life compared to polymers comprising 2,2'-linked spirobifluorene units is likewise unexpected, since these polymers are also partly conjugated and comprise similar units.

(2) The polymers of the invention have, at the same composition, higher light-emitting efficiencies at a high luminance in use. This is of tremendous importance, since it enables, on the one hand, the same brightness to be achieved at a lower energy consumption, which is of particularly great importance in mobile applications (displays for mobile telephones, pagers, PDAs, etc.) which are designed for batteries and accumulators. Conversely, higher brightnesses are obtained at a given energy consumption, which can be of interest, for example, for lighting applications.

(3) Particularly compared to 2,7-linked spirobifluorene polymers, a deeper blue emission colour can be achieved together with a sharper emission band. For this reason, the polymers of the invention are better suited than polymers of the prior art for copolymerization of another blue emitter, since the energy can be better transferred to the emitter as a result.

(4) Compared specifically to 2,7-linked spirobifluorene polymers containing triplet emitters, the polymers of the invention make it possible to achieve better energy transfer to the polymer and a lower back-transfer of energy to the remaining polymer. As a result, firstly pure emission colours and secondly a higher efficiency are obtained.

The present patent application text and also the examples below are directed at the use of the polymers of the invention in PLEDs and corresponding displays. Despite this restriction of the description, a person skilled in the art will readily be able to utilize, without having to make a further inventive step, the polymers of the invention as semiconductors (or in the case of suitable doping as conductors) for further uses in other electronic devices, e.g. inorganic field effect transistors (O-FETs), organic integrated circuits (O-ICs), organic thin film transistors (O-TFTs), organic light-emitting transistors (O-LETs), light-emitting electrochemical cells (LECs), organic solar cells (O-SCs), organic field quench devices (O-FQD, e.g. as described in M. Redecker et al. *Proc. 22$^{nd}$ International Display Research Conf.*, Nice 2002, pp. 97-99) or organic laser diodes (O-lasers). The use of the polymers of the invention in the corresponding devices is likewise subject matter of the present invention. The invention further provides organic field effect transistors (O-FETs), organic integrated circuits (O-ICs), organic thin film transistors (O-TFTs), organic solar cells (O-SCs), organic field quench devices (O-FQDs), organic light-emitting transistors (O-LETs), light-emitting electrochemical cells (LECs) and organic laser diodes (O-lasers) comprising at least one polymer according to the invention.

Likewise, a person skilled in the art will easily be able, without making a further inventive step, to apply the above descriptions of polymers to corresponding dendrimers or oligomers. Such dendrimers and oligomers are likewise subject matter of the present invention.

EXAMPLES

Example 1

Synthesis of Monomers which Lead to Units of the Formula (1) in Polymers

The synthesis of 4,4'-dibromo-1,1'-dimethoxyspirobifluorene (monomer M1) was carried out as described in the literature (X. Cheng et al., *Org. Lett.* 2004, 6, 2381-2383).

Example 2

Synthesis of Further Monomers

The synthesis of the monomers M2 to M5 is described in WO 03/020790 and the references cited therein. The synthesis of 2,2'-dibromospirobifluorene (monomer M6) which was used for the comparative polymer was carried out as described by F.-I. Wu et al. (*J. Mater. Chem.*, 2002, 12, 2893-2897). The structures of the further monomers for polymers according to the invention and comparative polymers are shown below.

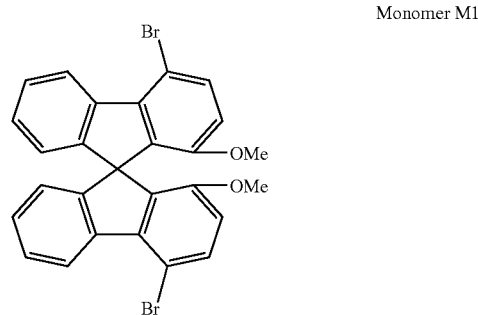

Monomer M1

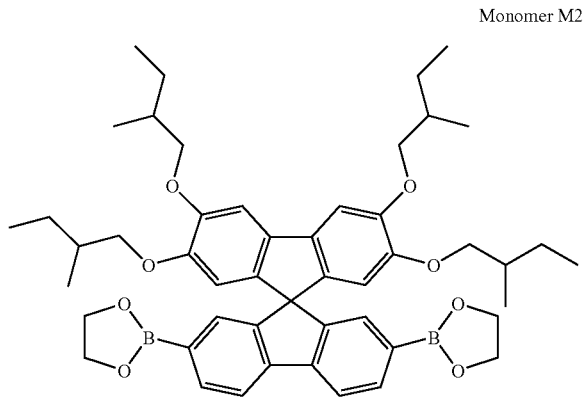

Monomer M2

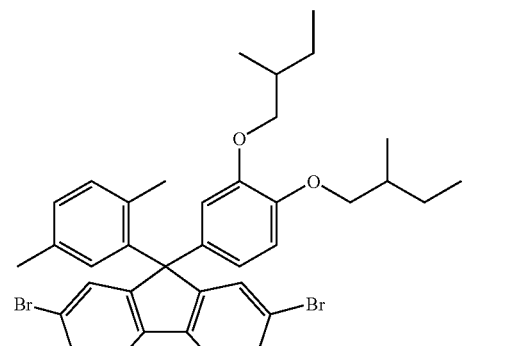

Monomer M3

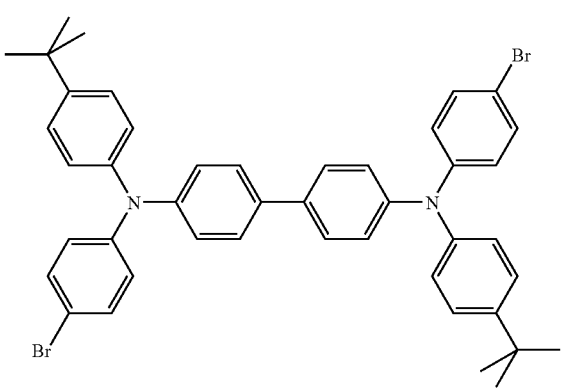

Monomer M4

-continued

Monomer M5

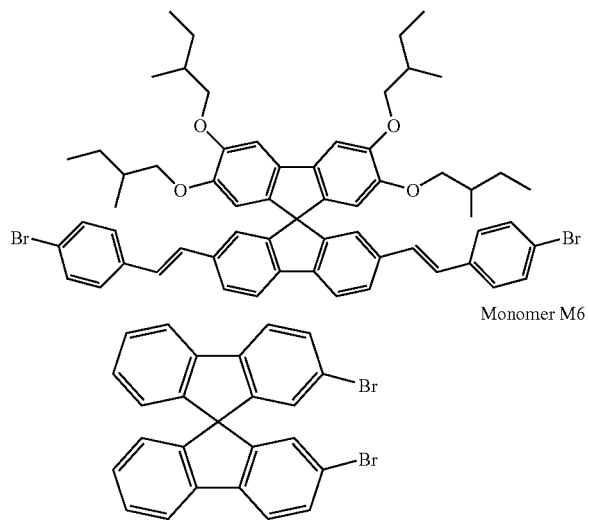

Monomer M6

PLEDs can be produced is comprehensively described in WO 04/037887 and the references cited therein.

Examples 5 to 10

Device Examples

The results obtained using the polymers P1 to P3 in PLEDs are summarized in Table 1. The electroluminescence results obtained using the comparative polymers C1 to C3 are likewise shown.

As can be seen from the results, the efficiency of the comparative polymers and the efficiency of the polymers according to the invention are comparable at low efficiency. However, at higher efficiency, the efficiency of the polymers according to the invention is significantly higher than that of the comparative polymers. This shows that the polymers according to the invention are better suited to use in displays having PM control than are polymers according to the prior art. In addition, the life of the polymers according to the invention under PM control is longer than that of the polymers according to the prior art under the same conditions.

TABLE 1

Device results obtained using polymers according to the invention and comparative polymers

| Example | Polymer | Monomer for units of the formula (1) | Further monomers | Max. Eff./ cd/A | Eff. @ 2000 cd/m²/cd/A | U @ 100 cd/m²/V | CIE x/y[a] | Life[b]/h |
|---|---|---|---|---|---|---|---|---|
| 5 | P1 | 10% M1 | 50% M2, 20% M3, 10% M4, 10% M5 | 4.54 | 3.9 | 3.9 | 0.17/0.30 | 450 |
| 6 | P2 | 30% M1 | 50% M2, 10% M4, 10% M5 | 4.08 | | 4.9 | 0.16/0.25 | 300 |
| 7 | P3 | 10% M1 | 50% M2, 30% M4, 10% M5 | 2.40 | | 3.8 | 0.16/0.24 | |
| 8 (comparison) | C1 | — | 50% M2, 30% M3, 10% M4, 10% M5 | 4.66 | 3.4 | 3.9 | 0.17/0.30 | 350 |
| 9 (comparison) | C2 | — | 50% M2, 20% M3, 10% M4, 10% M5, 10% M6 | 4.10 | | 4.0 | 0.17/0.29 | 340 |
| 10 (comparison) | C3 | — | 50% M2, 10% M3, 30% M4, 10% M5 | 2.29 | | 3.9 | 0.17/0.23 | |

[a]CIE coordinates: Colour coordinates according to the Commission Internationale de l'Eclairage 1931.
[b]Life: Time until the luminance has dropped to 50% of the initial luminance, MUX64 (100 Hz, pulse time: 156.25 μs, mean initial luminance: 400 cd/m², maximum peak luminance: 25600 cd/m²)

Example 3

Synthesis of the Polymers

The polymers were synthesized by SUZUKI coupling as described in WO 03/048225. The composition of the polymers P1 to P3 synthesized is summarized in Table 1. In addition, the comparative polymers C1 and C2 containing the monomer M3 or the monomer M6 instead of the monomer M1 which leads to units of the formula (1) in the polymer were synthesized. The composition of these comparative polymers is likewise shown in Table 1.

Example 4

Production of PLEDs

The polymers were examined for use in PLEDs. The PLEDs were in each case two-layer systems, i.e. substrate// ITO//PEDOT//polymer//cathode. PEDOT is a polythiophene derivative (Baytron P, from H. C. Starck, Goslar). Ba/Ag (Aldrich) was used as cathode in all cases. The way in which

The invention claimed is:

1. A polymer comprising (1) from 5 to 70 mol % of a first repeating unit of formula (I), Formula (1)

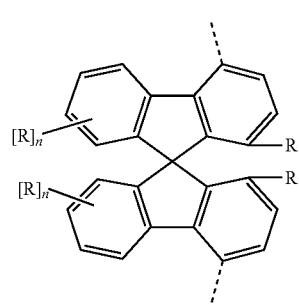

wherein
R identically or differently on each occurrence is F; Cl; Br; I; CN; $NO_2$; OH; $N(R^1)_2$; $Si(R^1)_3$; $B(R^1)_2$; a straight-chain alkyl, straight-chain alkoxy or straight-chain thioalkoxy group having up to 40 carbon atoms; or a branched or cyclic alkyl, branched or cyclic alkoxy or branched or cyclic thioalkoxy group having from 3 to 40 carbon atoms; wherein one or more nonadjacent carbon atoms in said straight-chain alkyl, straight-chain alkoxy, straight-chain thioalkoxy, branched or cyclic alkyl, branched or cyclic alkoxy, and branched or cyclic thioalkoxy groups is optionally replaced by —CR$^1$=CR$^1$—, —C≡C—, —NR$^1$—, —O—, —S—, —CO—O—, C=O, P(=O)R$^1$, SO, SO$_2$ or —O—CO—O0-, and wherein one or more H atoms is optionally replaced by fluorine, or an aromatic or heteroaromatic ring system having from 5 to 40 aromatic carbon atoms, wherein said aromatic or heteroaromatic ring system is optionally substituted by one or more nonaromatic radicals R; or a combination of 2, 3, 4, or 5 of these groups; and wherein two or more radicals R optionally define an aliphatic or aromatic monocyclic ring system or an aliphatic or aromatic polycyclic ring system;

R$^1$ identically or differently on each occurrence is H or an aliphatic or aromatic hydrocarbon radical having up to 20 carbon atoms;

n identically or differently on each occurrence is 0, 1, 2, 3, or 4; and the bonds shown as broken lines indicate the linkage in the polymer; and (2) from 95 to 30 mol % of a second repeating unit which is different from the repeating unit of formula (I).

2. A polymer according to claim 1, wherein:

R identically or differently on each occurrence is F; CN; NO$_2$; OH; N(R$^1$)$_2$; a straight-chain alkyl, straight-chain alkoxy, or straight-chain thioalkoxy group having up to 20 carbon atoms; or a branched or cyclic alkyl, branched or cyclic alkoxy, or branched or cyclic thioalkoxy group having from 3 to 40 carbon atoms; wherein one or more nonadjacent carbon atoms in said straight-chain alkyl, straight-chain alkoxy, straight-chain thioalkoxy, branched or cyclic alkyl, branched or cyclic alkoxy, and branched or cyclic thioalkoxy groups is optionally replaced by —CR$^1$=CR$^1$—, —C≡C—, —NR$^1$—, —O—, —S—, C=O or P(=O)R$^1$, and wherein one or more H atoms is optionally replaced by fluorine, or an aromatic or heteroaromatic ring system having from 5 to 30 aromatic ring atoms, wherein said aromatic or heteroaromatic ring system is optionally substituted by one or more nonaromatic radicals R; or a combination of 2, 3, or 4 of these groups; and wherein two or more radicals R optionally define an aliphatic or aromatic monocyclic ring system or an aliphatic or aromatic polycyclic ring system; and n identically or differently on each occurrence is 0, 1, 2, or 3.

3. A polymer according to claim 1, wherein said units of formula (I) are symmetrically substituted on the two spiro molecule halves.

4. A polymer according to claim 1, wherein said polymer is partially conjugated.

5. A polymer according to claim 1, further comprising additional repeating units, wherein said additional repeating units are aromatic, carbocyclic structures having from 6 to 40 carbon atoms and are optionally-substituted with radicals R, wherein R identically or differently on each occurrence is F; Cl; Br; I; CN; NO$_2$; OH; N(R$^1$)$_2$; Si(R$^1$)$_3$; B(R$^1$)$_2$; a straight-chain alkyl, straight-chain alkoxy or straight-chain thioalkoxy group having up to 40 carbon atoms; or a branched or cyclic alkyl, branched or cyclic alkoxy or branched or cyclic thioalkoxy group having from 3 to 40 carbon atoms; wherein one or more nonadjacent carbon atoms in said straight-chain alkyl, straight-chain alkoxy, straight-chain thioalkoxy, branched or cyclic alkyl, branched or cyclic alkoxy, and branched or cyclic thioalkoxy groups is optionally replaced by —CR$^1$=CR$^1$—, —C≡C—, —NR$^1$—, —O—, —S—, —CO—O—, C=O, P(=O)R$^1$, SO, SO$_2$ or —O—CO—O0-, and wherein one or more H atoms is optionally replaced by fluorine, or an aromatic or heteroaromatic ring system having from 5 to 40 aromatic carbon atoms, wherein said aromatic or heteroaromatic ring system is optionally substituted by one or more nonaromatic radicals R; or a combination of 2, 3, 4, or 5 of these groups; and wherein two or more radicals R optionally define an aliphatic or aromatic monocyclic ring system or an aliphatic or aromatic polycyclic ring system.

6. A polymer according to claim 5, wherein said additional repeating units are selected from the group consisting of fluorene derivatives; 2,7-spirobifluorene derivatives; dihydrophenanthrene derivatives; cis-indenofluorene derivatives; trans-indenofluorene derivatives; 1,4-phenylene derivatives; 4,4'-biphenylene derivatives; 4,4"-terphenylene derivatives; 2,7-phenanthrene derivatives; 3,6-phenanthrene derivatives; dihydropyrene derivatives; and tetrahydropyrene derivatives.

7. A polymer according to claim 1, further comprising structural elements which influence the morphology of the resulting polymers, optionally influence the emission color of the resulting polymers, wherein said structural elements are selected from the group consisting of unsubstituted fused aromatic structures having from 6 to 40 carbon atoms, R-substituted fused aromatic structures having from 6 to 40 carbon atoms, tolane derivatives, stilbene derivatives, and bisstyrylarylene derivatives; wherein R identically or differently on each occurrence is F; Cl; Br; I; CN; NO$_2$; OH; N(R$^1$)$_2$; Si(R$^1$)$_3$; B(R$^1$)$_2$; a straight-chain alkyl, straight-chain alkoxy or straight-chain thioalkoxy group having up to 40 carbon atoms; or a branched or cyclic alkyl, branched or cyclic alkoxy or branched or cyclic thioalkoxy group having from 3 to 40 carbon atoms; wherein one or more nonadjacent carbon atoms in said straight-chain alkyl, straight-chain alkoxy, straight-chain thioalkoxy, branched or cyclic alkyl, branched or cyclic alkoxy, and branched or cyclic thioalkoxy groups is optionally replaced by —CR$^1$=CR$^1$—, —C≡C—, —NR$^1$—, —O—, —S—, —CO—O—, C=O, P(=O)R$^1$, SO, SO$_2$ or —O—CO—O0-, and wherein one or more H atoms is optionally replaced by fluorine, or an aromatic or heteroaromatic ring system having from 5 to 40 aromatic carbon atoms, wherein said aromatic or heteroaromatic ring system is optionally substituted by one or more nonaromatic radicals R; or a combination of 2, 3, 4, or 5 of these groups; and wherein two or more radicals R optionally define an aliphatic or aromatic monocyclic ring system or an aliphatic or aromatic polycyclic ring system.

8. A polymer according to claim 1, further comprising structural elements which improve the hole injection properties and/or hole transport properties of the polymers, wherein said structural elements are selected from the group consisting of aromatic amines, aromatic phosphines, and electron-rich heterocycles.

9. A polymer according to claim 1, further comprising structural elements which improve the electron injection properties and/or electron transport properties of the polymers, wherein said structural elements are selected from the group consisting of electron-poor aromatics, heterocycles, and triarylboranes.

10. A polymer according to claim 1, further comprising structural elements which (1) improve the hole injection properties and/or hole transport properties of the polymers, wherein said structural elements are selected from the group consisting of aromatic amines, aromatic phosphines, and electron-rich heterocycles, and (2) improve the electron injection properties and/or electron transport properties of the polymers, wherein said structural elements are selected from the group consisting of electron-poor aromatics, heterocycles, and triarylboranes; and wherein the structural elements of (1) and (2) are bound to one another.

11. A polymer according to claim 1, further comprising structural elements which can emit light from the triplet state with high efficiency at room temperature.

12. A polymer according to claim 11, wherein said structural elements contain elements from groups 8, 9, and 10 of the periodic table of elements.

13. A polymer according to claim 11, wherein said structural elements improve the transition from the singlet state to the triplet state and are selected from the group consisting of carbazole derivatives, keto units, phosphine oxide units, sulphoxide units, sulphone units, and silane units.

14. A polymer according to claim 1, wherein said polymer further comprises at least 30 mol % of additional repeating units, wherein said additional repeating units are (1) aromatic, carbocyclic structures having from 6 to 40 carbon atoms and are optionally unsubstituted or substituted with radicals R, wherein
R identically or differently on each occurrence is F; Cl; Br; I; CN; $NO_2$; OH; $N(R^1)_2$; $Si(R^1)_3$; $B(R^1)_2$; a straight-chain alkyl, straight-chain alkoxy or straight-chain thioalkoxy group having up to 40 carbon atoms; or a branched or cyclic alkyl, branched or cyclic alkoxy or branched or cyclic thioalkoxy group having from 3 to 40 carbon atoms; wherein one or more nonadjacent carbon atoms in said straight-chain alkyl, straight-chain alkoxy, straight-chain thioalkoxy, branched or cyclic alkyl, branched or cyclic alkoxy, and branched or cyclic thioalkoxy groups is optionally replaced by $-CR^1=CR^1-$, $-C\equiv C-$, $-NR^1-$, $-O-$, $-S-$, $-CO-O-$, $C=O$, $P(=O)R^1$, SO, $SO_2$ or $-O-CO-O-$, and wherein one or more H atoms is optionally replaced by fluorine, or an aromatic or heteroaromatic ring system having from 5 to 40 aromatic carbon atoms, wherein said aromatic or heteroaromatic ring system is optionally substituted by one or more nonaromatic radicals R; or a combination of 2, 3, 4, or 5 of these groups; and wherein two or more radicals R optionally define an aliphatic or aromatic monocyclic ring system or an aliphatic or aromatic polycyclic ring system; and/or (2) selected from the group consisting of fluorene derivatives; 2,7-spirobifluorene derivatives; dihydrophenanthrene derivatives; cis-indenofluorene derivatives; trans-indenofluorene derivatives; 1,4-phenylene derivatives; 4,4'-biphenylene derivatives; 4,4"-terphenylene derivatives; 2,7-phenanthrene derivatives; 3,6-phenanthrene derivatives; dihydropyrene derivatives; and tetrahydropyrene derivatives.

15. A polymer according to claim 1, wherein said polymer further comprises at least 5 mol % of (1) structural elements which improve the hole injection properties and/or hole transport properties of the polymers, wherein said structural elements are selected from the group consisting of aromatic amines, aromatic phosphines, and electron-rich heterocycles, and/or (2) structural elements which improve the electron injection properties and/or electron transport properties of the polymers, wherein said structural elements are selected from the group consisting of electron-poor aromatics, heterocycles, and triarylboranes.

16. A polymer according to claim 1, wherein said polymers have random, alternating, or block structures or have one or more of these structures in an alternating sequence and wherein said polymers are linear, branched or dendritic.

17. A mixture comprising one or more polymers according to claim 1 together and one or more polymeric, oligomeric, dendritic, and/or low molecular weight substances.

18. A mixture according to claim 17, wherein said one or more polymeric, oligomeric, dendritic, and/or low molecular weight substances is a compound which can emit light from the triplet state at room temperature.

19. A solution or formulation comprising one or more polymers according to claim 1 in one or more solvents.

20. An electroluminescence material comprising one or more polymers according to claim 1.

21. An organic electronic device comprising one or more active layers, wherein said one or more active layers comprises one or more polymers according to claim 1.

22. An organic electronic device according to claim 21, wherein said organic electronic device is a polymeric light-emitting diode, an organic field effect transistor, an organic integrated circuit, an organic thin film transistor, an organic solar cell, an organic field quench device, an organic light-emitting transistor, a light-emitting electrochemical cell, or an organic laser diode.

* * * * *